United States Patent [19]

Hosaka et al.

[11] Patent Number: 4,788,142

[45] Date of Patent: Nov. 29, 1988

[54] METHOD OF ASSAYING THE METABOLIC ACTIVITY OF CELLS CAPABLE OF ENDOCYTOSIS

[75] Inventors: Shuntaro Hosaka, Kamakura; Takafumi Uchida, Tokyo, both of Japan

[73] Assignee: Toray Industries, Incorporated, Japan

[21] Appl. No.: 639,255

[22] Filed: Aug. 9, 1984

[30] Foreign Application Priority Data

Aug. 9, 1983 [JP] Japan ................. 58-145229

[51] Int. Cl.⁴ .............. C12Q 1/02; C12Q 1/04; C12Q 1/06; G01N 33/546
[52] U.S. Cl. ....................... 435/29; 435/34; 435/39; 436/531; 436/534
[58] Field of Search .............. 424/9; 435/29, 34, 39, 435/182, 948; 436/519, 523, 531, 829, 534

[56] References Cited

FOREIGN PATENT DOCUMENTS 8332404 6/1984 United Kingdom .

OTHER PUBLICATIONS

Boros, *Gradwohl's Clinical Laboratory Methods and Diagnosis*, vol. 2, 8th Edition, The C. V. Mosby Co., St. Louis, Mo., 1249–1256 (1980).

Chemical Abstracts, vol. 92 No. 213341y, p. 453 (1980).

Mirro et al., J. Immunological Methods vol. 47: pp. 39–48 1981.

R. Allen, et al., "Phagocytic Activation of a Luminol–dependent Chemi–luminescence in Rabbit Aleolar and Peritoneal Macrophages," *Biochem. Biophys. Res. Comm.* 69: 245–252 (1976).

R. Allen, et al., "Evidence for the Generation of an Electronic Excitation State(s) in Human Polymorphonculear Leukocytes and its Participation in Bactericidal Activity," *Biochem. Biophys. Res. Comm.* 47: 679–684 (1972).

*Primary Examiner*—Esther M. Kepplinger
*Attorney, Agent, or Firm*—Scully, Scott, Murphy & Presser

[57] ABSTRACT

The activity of cells is assayed by mixing the cells capable of endocytosis with microbeads 0.03–20 μm. in diameter containing a chemiluminecent substance and measuring the intensity of the luminescence generated by the action of highly reactive oxygen with the microbeads taken inside the cells.

6 Claims, 4 Drawing Sheets

METHOD OF ASSAYING THE METABOLIC ACTIVITY OF CELLS CAPABLE OF ENDOCYTOSIS

BACKGROUND OF THE INVENTION

The present invention relates to a method of assaying the activity of cells.

A variety of methods have hithertofore been applied for assaying the activity of cells.

Such methods have been adopted, for example, for examining chemotaxis, adhesiveness, phagocytosis, release of lysozomal enzymes and release of highly reactive oxygen of phygocytes such as macrophages, monocytes and granulocytes, cytotoxicity of phagocytes, lymphocytes, NK cells or Killer cells, release of lymphokine-like substances from phagocytes and lyphocytes, phagocytosis of platelet or the like.

The known methods of assaying the activity of cells are more or less disadvantageous in that they are not quantitative, simple enough or require use of radioisotopes.

R. C. Allen et al. in BBRC 47, 1972, 679-684 report assay of the bactericidal activity of polymorphonuclear leukocytes by a chemiluminescence of active oxygen. Strength of the chemiluminescence of active oxygen is measurable in itself but, the chemiluminescent response is so low that instruments of high sensitivity are required for the measurement. Combined use of a chemiluminescent is reported to overcome such difficulties (cf. R. C. Allen et al., BBRC 69, 245-252), which represents a simple and highly sensitive method without use of the radioisotope. Since the method, however, consists of addition of a chemiluminescent in solution, active oxygen released outside the cell is predominantly measured. Therefore, examination of the condition inside the cell, namely, inside the cell membrane or inside phagocytic cells is impossible.

SUMMARY OF THE INVENTION

It is an object of the present invention to provide a simple method of assaying the activity of cells safely and quantitatively.

The invention resides in a method of assaying the activity of cells which comprises mixing the cells with microbeads of a size 0.03-20 $\mu$m in diameter containing a chemiluminescent substance.

Use of the method of assaying the activity of cells enables examination of the activity of cells in a simple and quantitative manner. The method is very useful for the examination of the condition inside the cell membrane or inside phagocytic cells.

DESCRIPTION OF THE PREFERRED EMBODIMENTS

The cells used in the present invention may be any of those which are capable of carrying out endocytosis, which include phagocytes such as macrophages, granulocytes and monocytes and bone marrow cells, their precursors. Granulocytes (neutrophils, eosinophils and basophils) and monocytes may be collectively employed as leukocytes without fractionation. Another example of cells which is capable of carrying out endocytosis is platelet.

The endocytosis is a function of cells by which substances outside the cells are taken inside the cells through flowing and movement of the cell membrane.

As the microbeads may be employed natural or artificial ones of biological or non-biological origin. Examples of the one of biological origin are yeasts, particularly zymosan, bacteria and viruses. Those which have diameters in the range between 0.03 and 20 $\mu$m, preferably between 0.1 and 10 $\mu$m may be employed. The shape may be spherical or non-spherical. In cases where the shape is non-spherical, the diameter may be estimated as $\frac{1}{2}$ of the sum of maximum and minimum diameters for convenience' sake. Although the microbeads are desirably colorless, they may be colored provided that measurement of the luminescence is not disturbed.

Particular preferred material for the microbeads may be mentioned is synthetic macromolecular substances. As examples may be mentioned hydrophobic polymers such as polystyrene, polyacrylonitrile, polymethacrylonitrile, polymethyl methacrylate, poly-$\epsilon$-capramide and polyethylene terephthalate, and crosslinked hydrophilic polymers such as polyacrylamide, polymethacrylamide, poly-N-vinylpyrrolidone, polyvinyl alcohol, poly(2-hydroxyethyl methacrylate), poly(2,3dihydroxypropyl acrylate), poly(2,3-dihydroxypropyl methacrylate) and polyethyleneglycol methacrylate. The hydrophilic polymers include various copolymers in addition to the homopolymers as mentioned above. Examples of such copolymers are hydrolyzate of the copolymer of glycidyl methacrylate and methacrylic acid, hydrolyzate of the copolymer of methyl methacrylate and glycidyl methacrylate, and hydrolyzate of the copolymer of butyl methacrylate and glycidyl methacrylate.

Crosslinking of these hydrophilic polymers can be effected by the use as a comonomer a polyfunctional vinyl monomer such as, for example, ethyleneglycol dimethacrylate, diethyleneglycol dimethacrylate or triethyleneglycol dimethacrylate.

Among these polymers, the hydrophilic polymers are preferable because the particles are hardly agglutinative and the chemiluminescent substance taken inside the particle can be effective for the detection of oxidizing substances. Particularly desirable are hydrolyzates of the copolymers of glycidyl methacrylate and methacrylic acid together with the polyfunctional vinyl monomers as mentioned above. In addition, microbeads of a hydrophobic polymer coated on the surface with a hydrophilic polymer are an embodiment within the scope of the invention.

As the chemiluminescent substances used in the invention may be mentioned, for example, isoluminol derivatives such as N-(4-aminobutyl)-Nethylisoluminol, N-(6-aminohexyl)-N-ethylisoluminol and N-(4-aminobutyl)-N-ethylisoluminol hemisuccinamide, luminol, isoluminol, lophin, lucigenin, acrydinium esters, pyrogallol, lucipherine, indoles, riboflavin, thiazine dyes and the like.

Incorporation of the chemiluminescent substances in the microbeads may be effected either by chemical bonding or by physical adsorption. Chemical bonding, however, is preferable because the chemiluminescent substance is less releasable from the microbeads. The chemical bonding is by a covalent or by an ionic bond. In some instances by the covalent bond, quantum yield of the chemiluminescence is lower than that of free luminol. Even in such cases, the luminescent ability satisfactory for the desired use can be attained. Reduction in the luminescence efficiency by the formation of covalent bond is less with a chemiluminescent substance in which the amino group to be reacted with formyl group is remote from the chemiluminescent group such as in N-(4-aminobutyl)-N-ethylisoluminol. It is preferable that amount of the chemiluminescent substance combined with the microbeads is at least 50 cps/$\mu$g. Satisfactory chemiluminescence is produced with luminol in an amount of $10^{-10}$ mol/$\mu$g.

In a most preferred embodiment of the invention, a copolymerization is carried out with 85 mol% of glycidyl methacrylate, 10 mol% of methacrylic acid and 5 mol% of triethyleneglycol dimethacrylate, microparticles thus produced are hydrolyzed and treated with periodate to convert the vicinal hydroxyl groups to formyl groups, followed by reaction with luminol to form Schiff bases thereby obtaining microbeads in which the chemiluminescent substance is chemically combined.

When cells carry out endocytosis, metabolic actions of the cells become active and substances with high oxidative activities such as active oxygen and oxidized arachidonic acid are produced. Such substances are produced in the cell membrane. The present invention is directed to a method involving measurement of chemiluminescence produced when the microbeads with a chemiluminescent combined are attached to the cells or thereby introduced into the cells. Examinations can be made directly or indirectly by such measurement for the activity of cells such as phagocytic activity, bacteriocidal activity, cell-injuring activity (antitumoric activity), complement-producing activity, lymphokine-producing activity or prostaglanding-producing-activity.

There can be attached to the surface of microbeads immunoglobulin or a complement component, and hormones or lymphokines can also be attached.

Attachment of immunoglobulin on the surface of microbeads can be carried out, for example, by the method disclosed in Japanese Patent Laid Open No.141559/1981. Attachment of complement to the surface of microbeads can be carried out, for example, by the method disclosed in Japanese Patent Laid Open No.175128/1982. The fixation of hormones, lymphokines or cell-derived substances can also be carried out by the method disclosed in Japanese Patent Laid Open No.141559/1981.

Measurement of the luminescence is desirably made by means of an instrument capable of counting the generated photons such as a photon counter or scintillation counter.

EXAMPLE 1

Test on the Phagocytic and Bactericidal Activities of Mouse Peritoneum Macrophage using Luminol-Binding Microbeads Preparation of Luminol-Binding Microbeads Glycidyl methacrylate, 2-hydroxyethyl methacrylate, methacrylic acid and triethylene glycol methacrylate were mixed at a ratio of 65 : 20 : 10 : 5. To a solution of 24 g. of the monomer mixture in 76 g. of ethyl propionate was added 0.13 g. of 2,2'-azobis(2,4-dimethyl-4-methoxyvaleronitrile). The mixture was reacted under nitrogen atmosphere at 40° C. for 3 hours.

Particles (2 $\mu$m in diameter on average) thus precipitated were stirred in 0.3% aqueous solution of sulfuric acid at 30° C. for 10 days to hydrolyze the epoxy group in the particles.

In 1 ml. of water containing 10 mg. of $NaIO_4$ dissolved therein was dispersed 10 mg. of the hydrolyzed particles. After adjusting the pH to 4, the dispersion was reacted at room temperature for 1 hour. After washed, the particles were dispersed in 0.1N NaOH aqueous solution containing 1 mg. of luminol dissolved therein. The dispersion was reacted at room temperature for 2 hours. Excess luminol was removed by washing to obtain luminol-binding microbeads.

Isolation of Mouse Peritoneum Macrophage

Female BALB/C mouse was used, which was intraperitoneally injected with Freund's complete adjuvant 5 days previously to the isolation of macrophages. Cells were taken out of the peritoneum of the mouse, and the cells that were adsorbed on a plastic dish coated in advance with bovine newborn serum were collected to obtain macrophages.

The macrophages thus obtained were dispersed in an Eagle's MEM containing 10% of bovine fetus serum to a concentration of $10^7$ macrophages/ml.

Determination of Phagocytic and Bactericidal Activities of the Macrophages

The phagocytic and bactericidal activity was determined on the strength of chemiluminescence, which was measured by means of a biocounter-M2010 manufactured by LUMAC & Co.

In a plastic vial special for LUMAC was placed 100 $\mu$l. of the macrophage dispersion. The vial was placed in a sample room at 37° C. for 2 min., followed by addition of 100 $\mu$l. of the dispersion containing the luminol-binding microbeads at a concentration of $3 \times 10^9$/ml., and measureement of the chemiluminescence was initiated. The measurement was made at an interval of 1 min., each measurement being over 10 sec. to determine amount of the chemiluminescence per min.

Control experiments were run using (1) 100 $\mu$l. of a luminol solution at 20 $\mu$g./ml. in place of the luminol-binding microbeads; (2) 100 ul. of a luminol solution at 20 $\mu$g./ml. plus 100 $\mu$l. of a suspension of plain microbeads at 100 $\mu$g./ml.; and (3) a suspension of plain microbeads alone.

Results are shown in FIG. 1.

EXAMPLE 2

Test on the degree of macrophage activation using luminol-binding microbeads

Preparation of opsonized luminol-binding microbeads

Luminol-binding microbeads were prepared in the same way as in Example 1. To a dispersion of 10 $\mu$g. of the luminol-binding microbeads in 1 ml. of water was added 100 $\mu$g. of mouse IgG. To the mixture was added 10 mg. of 1-ethyl-3-(3-dimethylaminopropyl)carbodiimide while adjusting the pH to 4.5 with 0.1 N HCl. The mixture was reacted overnight at 4° C. After washed; fresh mouse serum was added followed by stirring at 37° C. for 15 min. to prepare opsonized luminol-binding microbeads.

Isolation of Macrophage

The mouse was used in the same way as in Example 1. In order to activate the macrophage, the mouse was intraperitoneally injected 4 days previously to isolation of the macrophage with 200 $\mu$g. of Freund's complete adjuvant or 200 $\mu$g. of a solution of the thioglycollate medium in PBS at a concentration of 10 mg./ml.

The macrophage was collected in the same way as in Example 1.

Determination of Phagocytic and Bactericidal Activity of the Macrophage

Phagocytic and bactericidal activities of the macrophage were assayed using the opsonized luminolbinding microbeads for (1) the non-activated mouse; (2) the thioglycollate-activated mouse; and (3) the Freund's complete adjuvant-activated mouse.

Results are shown in FIG. 2.

EXAMPLE 3

Test on the Phagocytic and Bactericidal Activity of Human Loukocytes

Human Blood Cells

A blood specimen was prepared by mixing healthy human peripheral blood with 3.8% solution of sodium citrate at a ratio of 9 : 1.

Luminol-Binding Zymosan

To 1 ml. of 1% dispersion of zymosan (*Saccharomyces cerevisiae*) was added 100 µl. of 25% aqueous solution of glutaraldehyde. The mixture was stirred at 25° C. for 1 hour. After washed with water, the zymosan was dispersed in 1 ml. of a luminol solution (in 0.05N aqueous NaOH at a concentration of 0.5 mg./ml.).

After allowed to stand overnight at room temperature, the dispersion was repeatedly subjected to centrifugal separation at 3000 rpm to remove excess luminol thereby preparing luminol-binding zymosan.

Determination of the Phagocytic and Bactericidal Activity

A mixture of 100 µl. of the human blood specimen ($3.5 \times 10^6$ leukocytes/ml.) and 100 µl. of the luminol-binding zymosan ($4 \times 10^8$ cells/ml.) was measured for luminescence at intervals. Measurement was made in the same way as in Example 1.

Results are shown in FIG. 3.

EXAMPLE 4

Test on the Phagocytic and Bactericidal Activity of Granulocytes (PMN)

Isolation of PMN

To a mixture of 20 ml. of healthy human peripheral blood and 2 ml. of 3.8% solution of sodium citrate was added 20 ml. of dextran T500 (PHARMACIA). The resulting mixture was allowed to stand at 37° C. for 30 min., followed by centrifugal separation at 400G at 20° C. for 30 min. Cells precipitated by the centrifugal separation (PMN) was dispersed in PBS at a concentration of $3.6 \times 10^6$ cells/ml.

Determination of the Phagocytic and Bactericidal Activity

A mixture of PMN ($3.6 \times 10^6$ cells/ml.) and 10 µl. of the luminol-binding microbeads ($2.5 \times 10^9$ particles/ml.) prepared in Example 1 was measured for luminescence at intervals.

Results are shown in FIG. 4.

BRIEF DESCRIPTION OF THE DRAWINGS

In FIGS. 1-2, the curves designated by the numbers 1-7 respectively represent:

Figure 1:
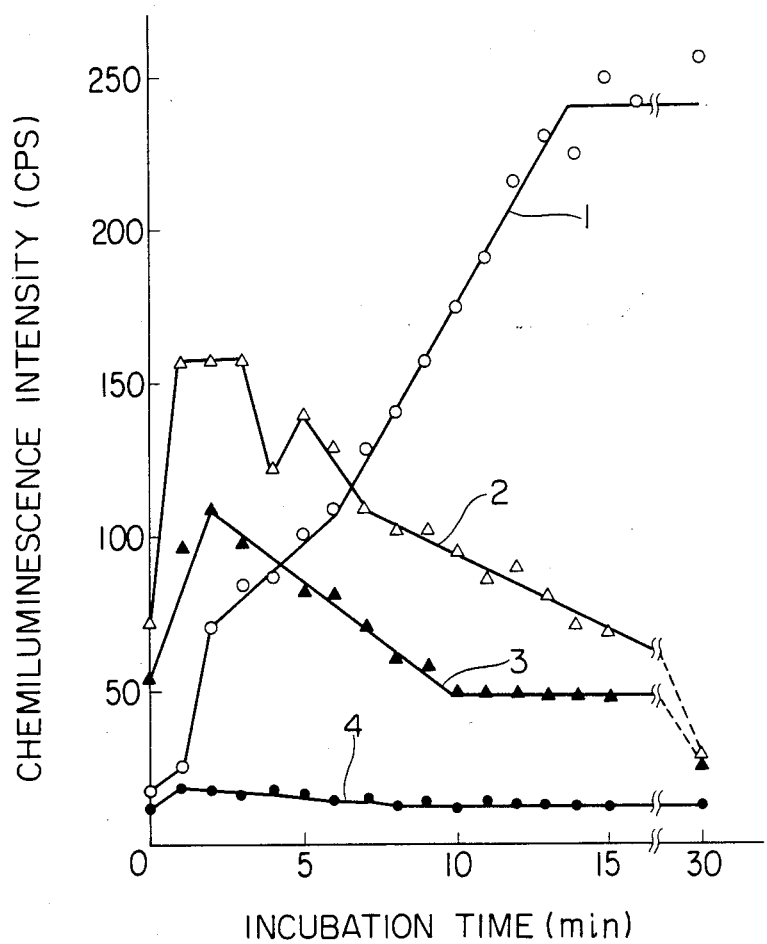
FIGS. 1-4 are graphs showing the test results obtained in Examples 1-4, respectively.
Figure 2:
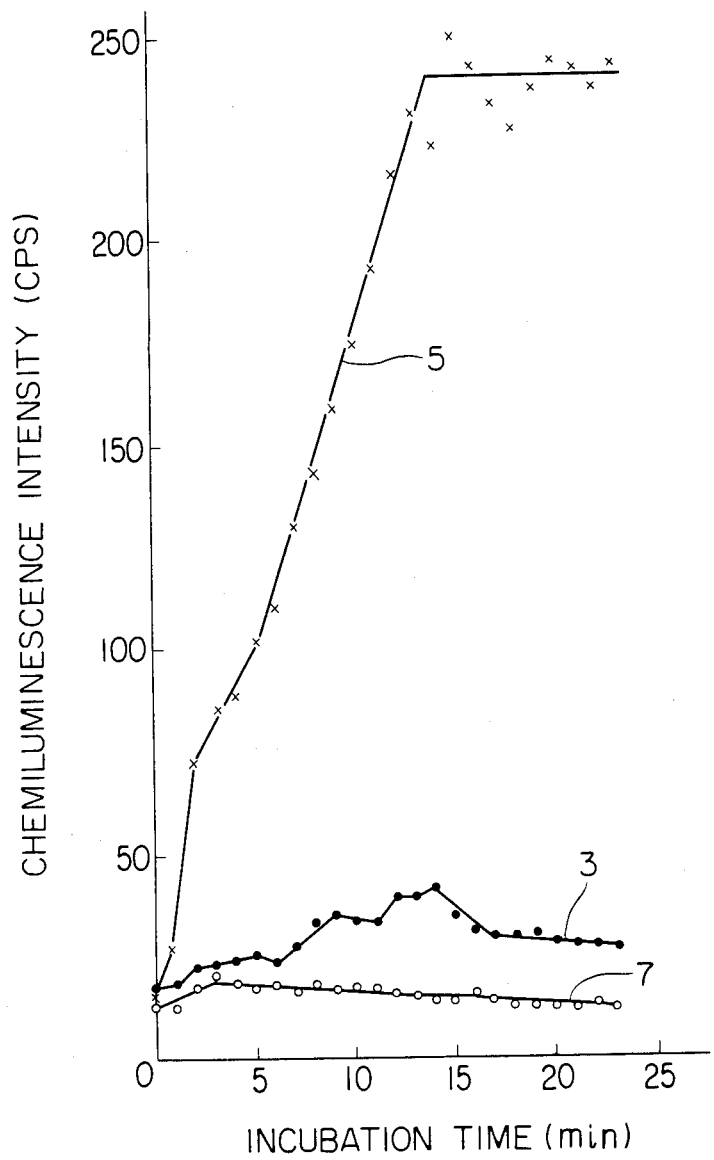
Figure 3:
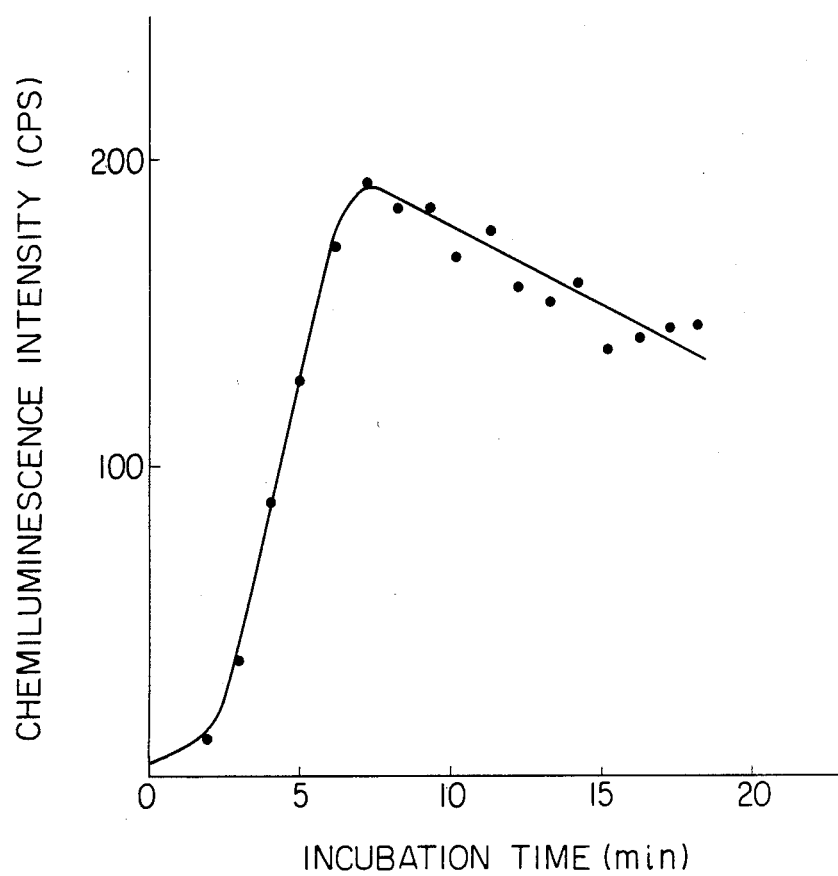
Figure 4:
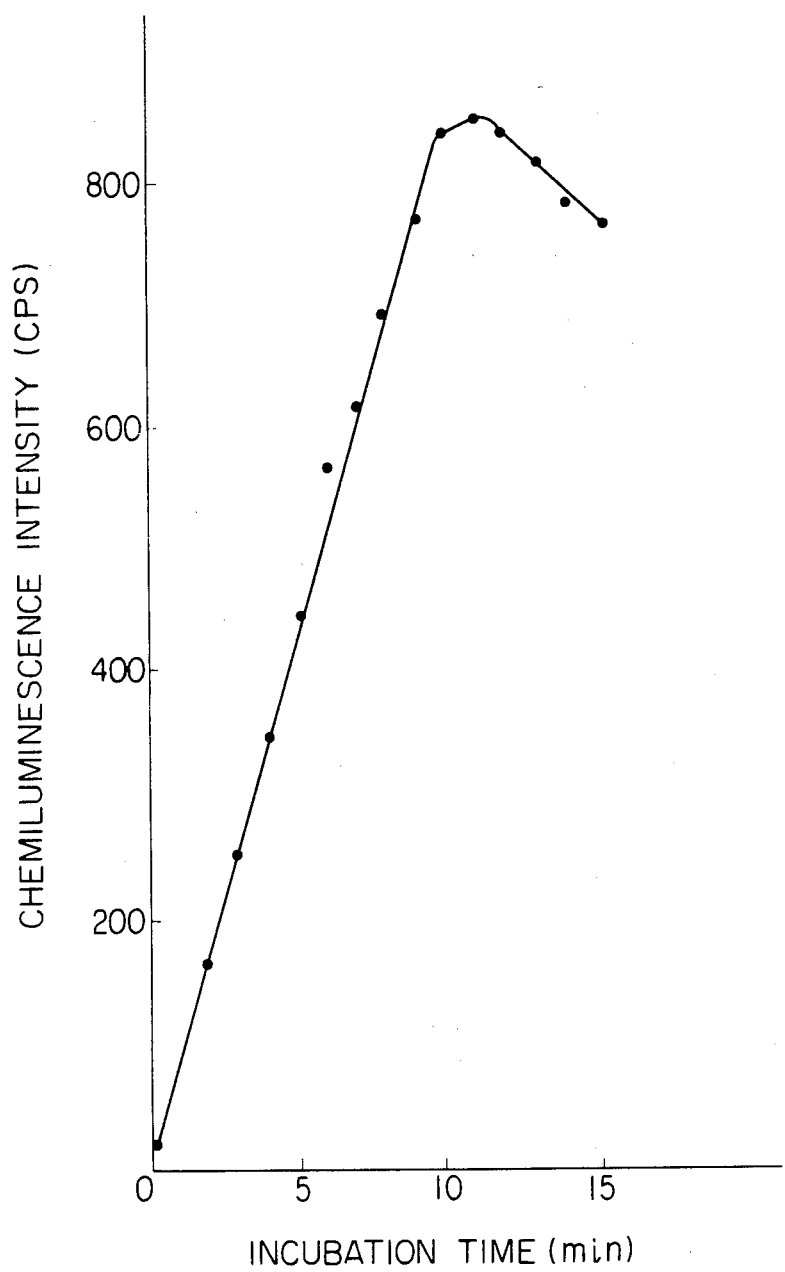

1 . . . use of the luminol-binding microbeads;
2 . . . use of the mixture of theluminol solution and the plain microbead dispersion;
3 . . . use of the luminol solution alone;
4 . . . use of the plain microbeads alone;
5 . . . measurement of the macrophages activated with Freund's complete adjuvant using the luminol-binding microbeads;
6 . . . measurement of the thioglycollate-activated microbeads using the luminol-binding microbeads; and
7 . . . measurement of the non-activated macrophage using the luminol-binding microbeads.

What is claimed is:

1. Method of assaying the cellular metabolic activity of cells capable of endocytosis which comprises mixing the cells with microbeads 0.03-20 um in diameter to which is bound a chemiluminescent substance capable of reacting with active oxygen in the cell and measuring intensity of the resulting luminescence wherein the cells are phagocytes or platelets.

2. The method according to claim 1 wherein the microbeads have a diameter of 0.1-10 um.

3. The method according to claim 1 wherein the phagocytes is macrophages, monocytes or granulocytes.

4. The method according to claim 1 wherein the chemiluminescent substance is luminol, isoluminol, an isoluminol derivative or lucigenin.

5. The method according to claim 1 wherein the chemiluminescent substance is bound to the microbeads by chemical bond.

6. The method of claim 1 wherein the microbeads comprise a hydrolyzate of a copolymer of glycidyl methacrylate and methacrylic acid.

* * * * *

UNITED STATES PATENT AND TRADEMARK OFFICE
CERTIFICATE OF CORRECTION

PATENT NO. : 4,788,142

DATED : November 29, 1988

INVENTOR(S) : Shuntaro Hosaka, et al.

It is certified that error appears in the above-identified patent and that said Letters Patent is hereby corrected as shown below:

Column 1, line 25: "47" should read as --47--

Column 1, line 31: "69" should read as --69--

Column 2, line 50: "Nethylisoluminol" should read as --N-ethylisoluminol--

Signed and Sealed this

Eleventh Day of July, 1989

Attest:

DONALD J. QUIGG

Attesting Officer

Commissioner of Patents and Trademarks